(12) United States Patent
Eisele

(10) Patent No.: US 9,060,774 B2
(45) Date of Patent: Jun. 23, 2015

(54) HIGH-FREQUENCY SURGICAL DEVICE

(75) Inventor: Florian Eisele, Freiburg im Breisgau (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 1563 days.

(21) Appl. No.: 11/883,073

(22) PCT Filed: Jan. 25, 2006

(86) PCT No.: PCT/EP2006/000645
§ 371 (c)(1),
(2), (4) Date: Aug. 17, 2007

(87) PCT Pub. No.: WO2006/079524
PCT Pub. Date: Aug. 3, 2006

(65) Prior Publication Data
US 2008/0147057 A1   Jun. 19, 2008

(30) Foreign Application Priority Data

Jan. 26, 2005 (DE) .......................... 10 2005 003 707
Jun. 6, 2005 (DE) .......................... 10 2005 025 946

(51) Int. Cl.
*A61B 18/12* (2006.01)
*A61B 18/00* (2006.01)
(Continued)

(52) U.S. Cl.
CPC ... *A61B 18/1206* (2013.01); *A61B 2018/00892* (2013.01); *A61B 5/05* (2013.01); *A61B 2017/00123* (2013.01); *A61B 2018/00702* (2013.01); *A61B 2018/00779* (2013.01)

(58) Field of Classification Search
CPC ............... A61B 18/12; A61B 18/1206; A61B 18/1233; A61B 2018/0016; A61B 2018/00214; A61B 2018/00642; A61B 2018/00666; A61B 2018/00702; A61B 2018/00708; A61B 2018/00827; A61B 2018/00875; A61B 2018/00892; A61B 2018/128; A61B 2018/1467
USPC .................. 606/32, 35–35, 37–42, 45, 48–50
See application file for complete search history.

(56) References Cited

U.S. PATENT DOCUMENTS 5,267,994 A * 12/1993 Gentelia et al. .................. 606/15
5,423,809 A *  6/1995 Klicek ............................ 606/38
(Continued)

FOREIGN PATENT DOCUMENTS

CN      1529569 A     9/2004
DE    38 38 840 A1     5/1990
(Continued)

*Primary Examiner* — Ronald Hupczey, Jr.
(74) *Attorney, Agent, or Firm* — Dickstein Shapiro LLP

(57) ABSTRACT

The invention relates to a high-frequency surgical device for monopolar coagulation of biological tissue using a high-frequency current. The device includes an electrosurgical instrument with a coagulation electrode and a surgical device with a high-frequency generator for generating a high-frequency voltage and for supplying the high-frequency current to the coagulation electrode of the electrosurgical instrument and at least one control device for terminating the coagulation process. A measuring device detects at least one measured value describing a measured tissue introduction of energy into a defined measured tissue area. An arithmetic device determines the measured tissue introduction of energy into the defined measured tissue area and a final value for a target tissue introduction of energy into a target tissue area. The control device regulates the high-frequency generator based on the final value by generating a shut-down signal when the target tissue introduction of energy reaches the final value.

25 Claims, 2 Drawing Sheets

(51) Int. Cl.
  *A61B 5/05* (2006.01)
  *A61B 17/00* (2006.01)

(56) References Cited

U.S. PATENT DOCUMENTS

| | | | |
|---|---|---|---|
| 5,542,916 A | 8/1996 | Hirsch et al. | |
| 5,817,093 A * | 10/1998 | Williamson et al. | 606/50 |
| 5,971,980 A * | 10/1999 | Sherman | 606/34 |
| 6,733,498 B2 * | 5/2004 | Paton et al. | 606/41 |
| 6,855,141 B2 * | 2/2005 | Lovewell | 606/34 |
| 6,855,142 B2 * | 2/2005 | Harano et al. | 606/40 |
| 7,678,105 B2 * | 3/2010 | McGreevy et al. | 606/32 |
| 7,722,601 B2 * | 5/2010 | Wham et al. | 606/34 |
| 2002/0026188 A1 | 2/2002 | Balbierz et al. | |
| 2002/0165530 A1 | 11/2002 | Harano et al. | |
| 2004/0030329 A1 | 2/2004 | Hagg | |
| 2004/0078038 A1 | 4/2004 | Desinger et al. | |
| 2005/0113819 A1 * | 5/2005 | Wham et al. | 606/34 |

FOREIGN PATENT DOCUMENTS

| | | |
|---|---|---|
| DE | 92 90 164 | 10/1994 |
| DE | 94 90 465 | 8/1996 |
| DE | 195 42 419 | 5/1997 |
| DE | 197 19 934 | 11/1997 |
| DE | 196 43 127 | 4/1998 |
| DE | 101 02 254 | 8/2002 |
| EP | 0 219 568 | 4/1987 |
| JP | 10-225462 A | 8/1998 |
| JP | 2001-522265 A | 11/2001 |
| WO | WO 93/03677 | 3/1993 |
| WO | WO 98/43547 A2 | 10/1998 |
| WO | WO 02/11634 | 2/2002 |

* cited by examiner

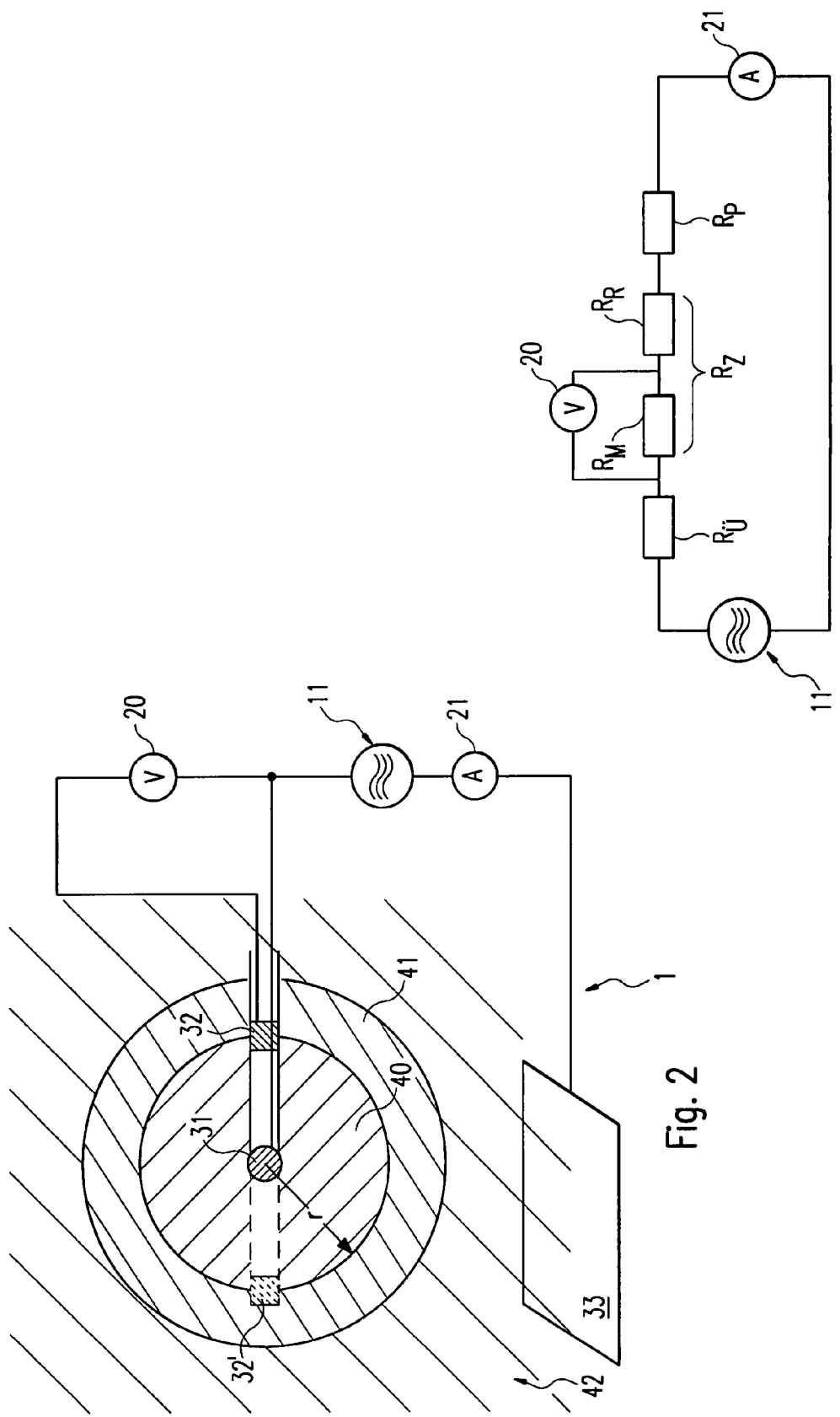

HIGH-FREQUENCY SURGICAL DEVICE

FIELD OF THE INVENTION

The invention relates to an HF (high-frequency) surgical device.

BACKGROUND OF THE INVENTION

High-frequency surgery has been used for many years in both human and veterinary medicine to coagulate and/or cut biological tissue. Hereby, suitable electrosurgical instruments are used to direct high-frequency ("HF") current through the tissue to be treated so that it changes as a result of protein coagulation and dehydration. The tissue contracts in such a way that the vessels are occluded and bleeding stopped. A subsequent increase in the current density achieves an explosion-like vaporisation of the tissue fluid and the ripping open of the cell membranes, wherein the tissue is completely transected.

Both bipolar and monopolar techniques are used for the thermal treatment of biological tissue. With monopolar arrangements, the HF current supplied by the HF generator to the electrosurgical instrument is applied to the tissue to be treated via an active electrode, wherein the current path passing through a patient's body travels to a neutral electrode and from there back to the HF generator. A high current density per unit of area to be treated is provided at the active electrode, while the current density per unit of area at the neutral electrode is much lower than that at the active electrode. This is achieved by means of a suitably large-area design of the neutral electrode. This is the only way to guarantee that no damage, such as burning, for example, occurs to the tissue on the passage of the current from the tissue to the neutral electrode.

Bipolar instruments with two electrode parts electrically insulated from each other are also increasingly gaining in importance. This means the current path between the electrode parts can be calculated and does not travel long distances through the patient's body. This reduces the influence of, for example, cardiac pacemakers or other devices connected to the patient during an operation.

Monopolar technology is in particular suitable for interstitial coagulation if a current that passes uniformly (e.g., with radial symmetry) through the tissue to be treated, i.e., through the target tissue, is required for the treatment. This enables the treatment of e.g., tumours or metastases in that the electrosurgical instrument suitable for the monopolar coagulation is inserted (stuck) into the tissue to be treated, for example into a tumour, and the destruction of the tumour (tumour devitalisation) is initiated by the application of the high-frequency current, that is by the coagulation.

Coagulation and/or a cutting process is performed using HF surgical devices comprising an HF surgical device with an HF generator to generate a high-frequency voltage, and hence a high-frequency alternating current, and switching devices and/or a control and regulating device to activate or deactivate the HF generator.

With monopolar coagulation, in particular with interstitial coagulation, but also with cutting processes, up to now it has not been possible to determine or assess the size of a coagulation zone in advance, since coagulation cannot be controlled in this regard. Instead, the size of the expected coagulation zone has to be estimated on the basis of empirical values and/or monitored using imaging techniques.

However, working exclusively with empirical values requires an increased safety factor to be observed with regard to the amount of energy to be introduced into the tissue. It is only with an excess of energy—together with the high stress this places on the tissue surrounding the target tissue—that the risk of incomplete coagulation, and hence incomplete devitalisation of the target tissue, can be avoided. Neither does the use of imaging techniques represent a satisfactory solution. On the one hand, imaging techniques are extremely complicated and cost-intensive, on the other hand, they cannot in principle be used with an HF current application.

The invention is therefore based on the object of further developing an HF surgical device of the type described above such that coagulation processes and/or cutting processes are optimised and can be monitored in an extremely simple way.

BRIEF DESCRIPTION OF THE DRAWINGS

The following describes the invention with reference to examples of embodiments which are described in more detail with reference to the following figures:

FIG. 2 is a simplified representation of a section of the functional block diagram of FIG. 1 according to the disclosed embodiments.

FIG. 3 is an equivalent circuit diagram, describing the mode of operation of the arrangement of FIGS. 1 and 2 with the aid of virtual components, according to the disclosed embodiments.

DETAILED DESCRIPTION OF THE INVENTION

Figure 1:
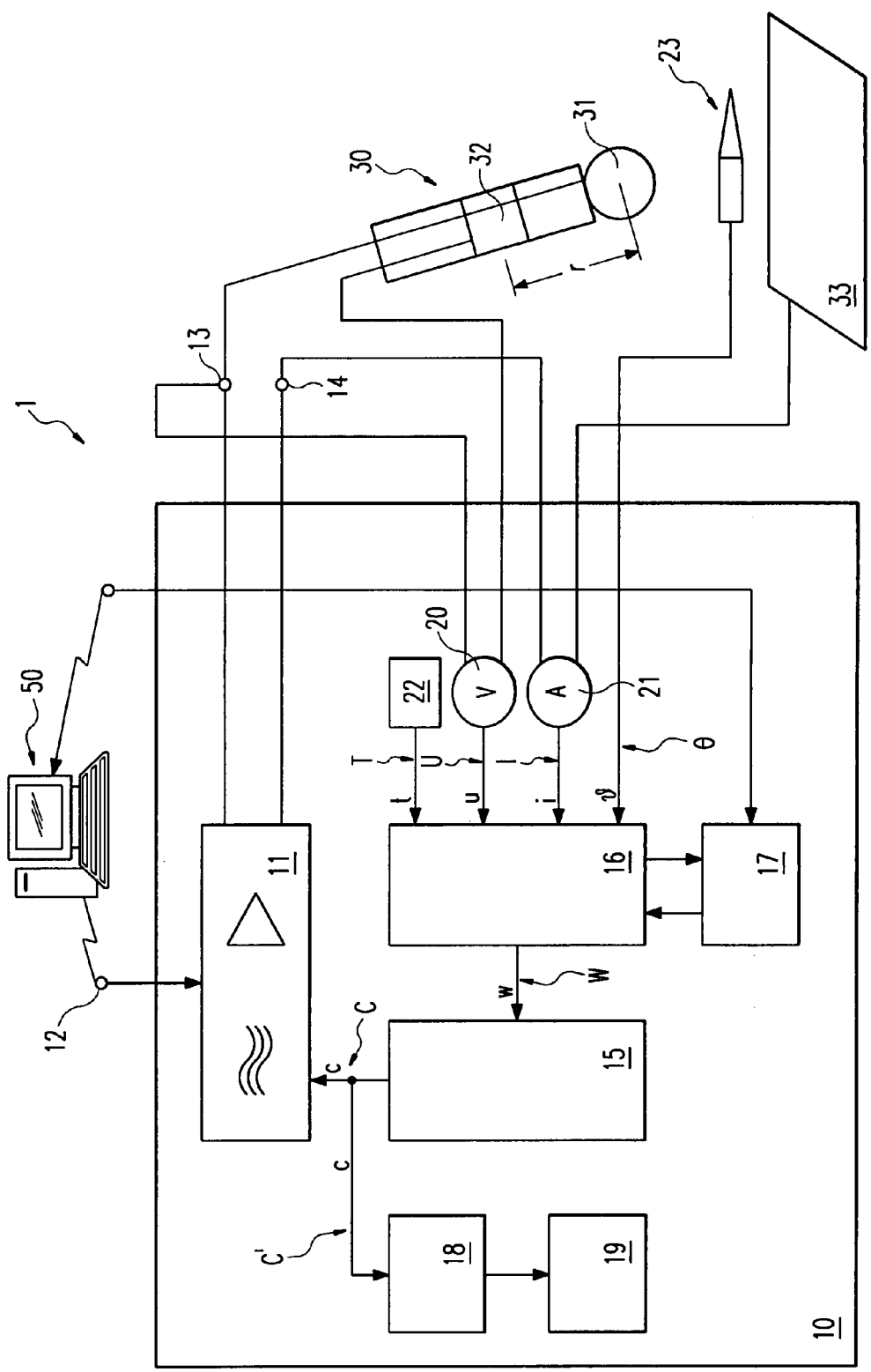
FIG. 1 is a functional block diagram representing an embodiment of the HF surgical device according to the disclosed embodiments.

The object is achieved by using an HF surgical device for the treatment, in particular for the monopolar coagulation of biological tissue using an HF current, wherein the HF surgical device comprises an electrosurgical instrument with a coagulation electrode and an HF surgical device with an HF generator for generating an HF voltage and for supplying the HF current to the coagulation electrode of the electrosurgical instrument and with at least one control device for terminating the coagulation process. A measuring device is assigned to the control device, said measuring device being designed in such a manner, that it detects at least one measured value describing a measured tissue introduction of energy into a defined measured tissue area. In addition, an arithmetic device is assigned to the control device, said arithmetic device being designed in such a manner, that it determines the measured tissue introduction of energy into the defined measured tissue area and that it determines a preset final value for the coagulation process for a target tissue introduction of energy into a target tissue area and/or adopts it as a stored final value. The control device is configured in such a manner that it controls or regulates the HF generator based on the final value in such a manner that the required HF current is supplied to the target tissue area and that it generates a shut-down signal when the target tissue introduction of energy reaches the final value.

The following describes the subject matter of the invention in particular with reference to a monopolar coagulation process. However, it is noted that the subject matter can in principle also be used with cutting processes, in particular with the coagulation associated therewith. The invention also relates to bipolar methods.

An essential point of the invention is to provide the HF current required for an optimum coagulation and/or cutting result in the tissue to be treated, the target tissue area, in that at least one measured value characteristic for the measured tissue introduction of energy into the measured tissue area is measured and an introduction of energy is determined therefrom in order on the basis of this and/or of empirical values to control or regulate the HF generator in such a manner that the introduction of energy required for the optimum coagulations and/or cutting result is achieved by matching the introduction of energy to the preset or determined final value for the target tissue introduction of energy into the target tissue area.

The difference between the measured tissue area and the target tissue area, as the tissue to be treated in the end, demonstrates that in principle it is possible to measure in an area which does not correspond to the area of tissue to be treated. This simplifies the measurement, and the components of the measuring device receiving the measured value can be attached to the tissue to be treated independently of the dimensions of the target tissue area. Since, a 'measurement' of the target tissue area tends to be rather difficult, as a rule a measurement is performed in the measured tissue area. Insofar, in the following description, a differentiation is made between the two areas. However, reference is made to the fact that in principle it is also possible to speak of a measured tissue area when this corresponds to the target tissue area because in this case the target tissue area is the measured tissue area. However, in all cases the measurement is performed in the tissue, that is, not on the actual generator (under distortion by line impedances, etc).

It is necessary to determine the introduction of energy into the measured tissue area (possibly also into the target tissue area) because unavoidable energy losses, for example thermal losses over the tissue areas surrounding the measured tissue area or the target tissue area (for example, tissues near a neutral electrode) or also an electrical power loss, caused, for example, by stray currents, cannot really be detected. A total introduction of energy introduced via the coagulation electrode is generally not fully available for the target tissue area due to these losses. The measuring device described herein is based on 'measuring' at least the measured tissue area so that in the end it is possible to assess how much introduction of energy will be retained for the target tissue area, for example.

Therefore, an introduction of energy into the measured tissue area is determined in order to draw conclusions therefrom about the required introduction of energy into the target tissue area. The required introduction of energy into the target tissue area can, for example, be determined by 'extrapolation' from the introduction of energy already made into the measured tissue area to the required introduction of energy into the target tissue area (taking into account the above-described losses). The measured value therefore serves as a basis for the determination of the required introduction of energy, wherein it is possible to determine, for example on the basis of the measured value, the amount of energy which must have already taken effect in the target tissue area and the amount of energy lost through surrounding tissue areas. The loss must be compensated in the determination of the required introduction of energy into the target tissue area, without placing additional stress on the tissue. The required introduction of energy for the target tissue area can however also be specified 'externally' and, on the basis of the measured value or of the actual introduction of energy into the measured tissue area, the introduction of energy still required for the optimum treatment of the target tissue area can take place on the basis of the control or regulation of the HF generator. Preferably, the determination of the required introduction of energy into the target tissue area is performed on the basis of empirical values, wherein the above-described losses are also taken into account.

The final value for the target tissue introduction of energy is in principle preset, since it is based for example on empirical values and/or determined from current tissue parameters. Therefore, the measured tissue introduction of energy provides an actual value, which is to be matched by an appropriate control or regulation to the final value, that is, to a set value. The actual value of the measured tissue introduction of energy has a functional relation with the measured value. To be more precise, this means that the actual value for the measured tissue introduction of energy can be determined from a actual value for the measured size. The actual value for the measured tissue introduction of energy must then be matched to the required final value for the target tissue introduction of energy. Thereby, the HF generator, and hence the HF current, is controlled or regulated in such a manner that the actual value (that is the introduction of energy into the measured tissue area) follows the possibly changing final value and to be precise until the final value for the target tissue introduction of energy required for the optimal coagulation process is achieved. As soon as the final value is achieved, the control device generates a shut-down signal which effects or enables the termination of the coagulation process. It is obviously also possible to display the actual value and control/switch off the generator manually. It is, therefore, in principle also possible to perform the control/switching-off on the basis of the determination of the measured value and/or the introduction of energy already made which may be determined therefrom.

In principle, the final value for the target tissue introduction of energy can be determined from the measured value in the measured tissue area or from the measured values, e.g., by means of extrapolation. This means that the measured value or the measured values should be used to extrapolate the required introduction of energy for the target tissue area. This is in particular easily possible when the measured tissue area corresponds to the target tissue area. However, to make a current regulation more precise, it is however advisable in practice to determine the final value at least additionally with reference to empirical values, which include the above-described losses, for example. The empirical values are available for example from experiments or from previous interventions and take into account tissue parameters for previously-measured tissue types which are as similar as possible to the tissue to be treated. This enables final values to be specified as set values, to which the introduction of energy into the measured tissue area as the instantaneous actual value is to be matched by the current regulation (control), in order finally to obtain the required introduction of energy into the target tissue area. The latter is in particular then recommended if the measured tissue area differs from the target tissue area.

For the determination of the introduction of energy, it is necessary, inter alia, for the current through the measured tissue area and the falling voltage over the measured tissue area to be known. The current through the measured tissue area is equal to the generator current (leakage currents are negligible with the voltages usually used for coagulation) and can be detected with conventional methods in the surgical device. The voltage over the measured tissue area on the other hand is not automatically available because, due to the above-described losses, it differs from the output voltage of the surgical device by a voltage drop which is additionally caused by the HF current in particular in the 'other structures' outside the measured tissue area or target tissue area. This voltage drop is therefore caused, for example, by patient resistance, but also by a transfer resistance, which occurs between the coagulation electrode and the target or measured tissue area.

Here, the term 'patient resistance' means the 'other structures', that is the tissue which is not to be treated, which is present between the defined target tissue area and the neutral electrode as a current path, and possibly a further transfer resistance between this tissue and the neutral electrode attached to the patient.

If in addition to the measurement of voltage and current, the power introduced into the target tissue is taken into account, it may be advantageous to determine the time required for the application of the power, since this 'energy inflow' together with the above-described losses through the surrounding tissue (='energy outflow') is decisive for the formation of the temperature gradients. The temperature gradient is in turn decisive for the question of ultimate interest regarding the place in where a temperature sufficient for the devitalisation is achieved.

In the event of thermal devitalisation by the HF current, the amount of energy corresponds to the converted electrical power integrated in the measured or target tissue area over time.

In a first preferred embodiment, an arithmetic device is designed in such a manner that the final value for the target tissue introduction of energy is re-determined repeatedly in defined time intervals so that this is specified in accordance with a fixed time sequence of a time-program control. The time-program control is required, for example, if the tissue area to be treated is to be observed during the coagulation process and its tissue changes are taken into account or if it is known from experience that the set value needs to be constantly adjusted during the coagulation. In this way, the changing tissue parameters during the coagulation form the basis for the further course of the coagulation. This means that the optimum final value for the target tissue introduction of energy can change during the course of the coagulation in such a manner that the repeated redetermination of the final value, which the actual value should follow, is required.

The time-program control can alternatively be provided in such a manner that a fixed time-program control is specified in advance, for example on the basis of empirical values, wherein the course of the coagulation in the tissue to be treated for example is not taken into account. This means that the arithmetic device is designed in such a manner that the final value for the target tissue introduction of energy is read from a preset set value progression. A combination of current tissue parameters with preset empirical values is also recommended in order to achieve the optimal introduction of energy in the tissue to be treated.

A time-program control facilitates in a simple way the regulation of the power input or of the introduction of energy taking into account the tissue changes or expected tissue changes.

Preferably, the measured tissue area is smaller than the target tissue area so that the components of the measuring device required to 'measure' the measured tissue area can be positioned independently of the dimensions of the target tissue area in the tissue to be treated. The determination of losses, which would occur in the target tissue area, could then be determined with the above-described empirical values. If the measured tissue area is identical to the target tissue area, and therefore the target tissue area is measured directly, the components of a measuring device recording the measured value should be placed exactly in the target tissue area. This requires knowledge of the precise extension of the target tissue area, which may be determined by imaging methods, for example.

Preferably, the measuring device comprises at least one measuring electrode arranged at a defined distance to the coagulation electrode, which may be brought into electrically conductive contact with the tissue to be treated in the measured tissue area, and at least one voltage-measuring device for measuring a dropping voltage over the measured tissue area, independently of any line losses or similar losses. For example, a power introduced into the measured tissue area can be determined from the measured values by the arithmetic device in order again to draw conclusions from this with regard to the final value for the target tissue introduction of energy.

The measuring electrode serves as a contact surface for the tissue to be treated and so, together with the coagulation electrode, defines the measured tissue area, at least in one direction; the measuring electrode lies in the current path that extends towards the neutral electrode. The voltage-measuring device is switched between the coagulation electrode and the measuring electrode in such a manner that the voltage drop over this measured tissue area can be determined. The contact surface is therefore connected by a measuring lead to the voltage-measuring device between this measuring point and the coagulation electrode, that is, the power-supplying, active electrode. This means that at least the voltage drop in the measured tissue area detected in this way serves as a basis for the determination of the measured tissue introduction of energy into the measured tissue area and possibly for the determination of the required introduction of energy into the target tissue area, in that the measured value is 'extrapolated' to the required introduction of energy into the target tissue area. The measured tissue introduction of energy can however also merely provide an indication of the energy which still needs to be introduced into the target tissue area in order to achieve the required introduction of energy. This means that the measured value or the determined measured tissue introduction of energy serves for example as a comparative value. The value of the required introduction of energy into the target tissue area is then specified 'externally' for example, wherein the comparative value demonstrates how much energy still has to be introduced into the target tissue area.

With this embodiment, the resistance determined through the tissue to be treated, that is through the defined target tissue area, may be understood in an equivalent circuit diagram as being connected in series with the above-described transfer resistance between the coagulation electrode and the target tissue area and with the patient resistance. When the measurement is preferably performed in the measured tissue area, which is smaller than the target tissue area, the resistance of the defined target tissue area is divided into a resistance of the measured tissue area and a saturation resistance, resulting from the remaining target tissue area. The embodiment provides that only the voltage drop of the source voltage caused by the coagulation process over the measured tissue area is detected in order to draw conclusions from this regarding to the introduced power and finally regarding the required introduction of energy into the target tissue area, which represents a particularly simple measuring method. This is insofar possible if—as described above—the corresponding current can be detected in the surgical device. However, generally the transfer resistance should also be taken into account. If the transfer resistance is correspondingly high and hence not negligible, the voltage drop caused by the transfer resistance must be included in the determination of the final value for the target tissue introduction of energy for correction.

If it is ensured, for example by cooling the electrode, by contact-establishing fluids flowing out of the electrode into the tissue or by the adaptation of the electrode shape (pressure) to the tissue, that the transfer resistance between the electrode and the measured tissue area remains small compared to the measured tissue resistance, the measurement of the voltage over the measured tissue area can be restricted to a measurement of the peak value and there is no need to determine the final value for the introduction of energy. This exploits the fact that as the coagulation of the defined measured tissue area advances, its resistance increases. Restriction to a measurement of the peak value has the advantage that the work for the measuring device is significantly simplified in particular when using non-sinusoidal coagulation voltages.

To measure the voltage drop over the measured tissue area or the target tissue area, it is alternatively possible to introduce a separate measuring current, for example via an additional electric circuit (e.g., a multiplexer) into the measured tissue area so that a voltage drop over the measured tissue area caused by this measured current can be measured as a measure for the impedance of the measured tissue (and hence of the target tissue).

Preferably, the measuring device further comprises at least one current-measuring device for measuring the HF current in the measured tissue area for the determination of the final value for the target tissue introduction of energy by the arithmetic device. As described above, the current through the measured tissue area corresponds to the generator current and can be detected in the surgical device using conventional technology. It is also possible to use an additional current-measuring device for measuring the measured tissue area in order to simplify the detection of the current occurring in the measured tissue area and to exclude faulty calculations due to leakage currents. It is also possible to extrapolate line losses in particular due to capacitive coupling between the lines by determining the phase displacement.

In a preferred embodiment, the measuring device further comprises at least one first time-measuring device for measuring the duration of the current flow into the measured tissue area for the determination of the final value for the target tissue introduction of energy by the arithmetic device. In addition, it is possible for the measuring device to comprise at least one second time-measuring device for measuring the duration of the measured tissue introduction of energy into the measured tissue area so that the final value for the target tissue introduction of energy can be determined by the arithmetic device in dependence on the duration of the measured tissue introduction of energy. As described above, it can be advantageous also to determine the time required for the application of the power, in particular, and not only the determination of work introduced. For example, a high power input into the measured and hence into the target tissue area over a shorter duration may have a different impact on the degree of coagulation of the tissue than a lower power input over a longer time interval, even if both power inputs perform the same work. A high power input over a short duration could possible cause a high degree of coagulation and hence unnecessary damage to the tissue to be treated or even to the surrounding tissue. Vice versa, a power input which is too low can permanently prevent an adequate degree of coagulation, even if the power input takes place over a lengthy period. Therefore, the detection of the time in which the power input takes place can enable the course of the coagulation to be better calculated.

It may be advisable to perform the coagulation at intervals as is provided, for example, with a thawing process with the aid of a microwave. The tissue is therefore heated for short intervals and excess heat is used for further coagulation during the interruption to the coagulation process.

As mentioned above, the final value for the target tissue introduction of energy into the target tissue area may be determined by extrapolation, for example or by extrapolation supported by empirical values. Empirical values are also required to draw conclusions from the measured tissue area regarding possible energy losses in the target tissue area. The empirical values required for this are preferably already available for types of tissue similar to the tissue to be treated. The measuring device is therefore assigned a storage device for the storage of experimentally determined measured values describing a series of measurements on comparative sample tissue so that the stored series of measurements can be used as the basis for the determination of the final value of the target tissue introduction of energy by the arithmetic device. Consequently, it is simple to refer to the experimentally obtained empirical values of tissue properties which ultimately reflect the coagulation behaviour of certain types of tissue. For example, taking into account the tissue dimensions, the thermal capacities or thermal conductivities allow conclusions to be drawn regarding the coagulation behaviour of the tissue to be treated. Preferably, measurement series with an extremely wide range of tissues for corresponding interventions should be available, which could be stored, for example, in the HF surgical device described here. In this way, during an intervention, the experimentally obtained data can be included in the calculation and determination procedure of the above-described measuring device and arithmetic device. For the determination of the final value, the empirical values used in this way offer a higher precision for the coagulation process than would be the case when using the empirical values described in the introduction without taking into account the measurements.

The control device is preferably assigned a further measuring device, which is designed in such a manner that the measured values describing the tissue to be treated can be measured and stored as comparative values in the storage device. This means that these measured values from the tissue to be treated can be accepted and stored before or even during an operation and possibly even afterward and are in this way available for further interventions. In addition, the tissue to be treated can be used directly for the above-described time-program control so that new final values are produced for the target tissue introduction of energy (set values) from tissue parameters which change during the coagulation. To facilitate the acceptance of the tissue parameters, the control device is assigned an input unit, which is designed in such a manner that a user can enter the measured values describing a comparative sample tissue and/or known tissue parameters for storage in the storage device. Preferably, the above-described further measuring device is designed in such a manner that the measured values detected on the tissue to be treated are automatically accepted in the storage device.

The observation of a temperature change in the measured tissue area may be useful for tracking the amount of heat introduced into the measured tissue area. For this, the measuring device further comprises at least one temperature-measuring device for measuring a tissue temperature in the measured tissue area. The measuring device is therefore designed in such a manner that the final value for the target tissue introduction of energy can be determined and/or corrected in dependence on the measured temperature or in dependence on the measured temperature and the stored series of measurements by the arithmetic device. The more data available for the determination of the final value, the more precisely the final value required for the optimum coagulation required final value for the introduction of energy can be determined. In particular, the observation of the temperature may enable, for example, conclusions to be drawn regarding a suitable or unsuitable power input and also regarding the degree to which the tissue has reached a temperature sufficient for devitalisation. When using two temperature-measuring devices, it is possible to determine a temperature gradient in the measured tissue area in order to understand the coagulation process even more exactly.

In addition, it is possible to draw conclusions regarding 'conditions' on the coagulation electrode, for example whether the electrode is still sufficiently free of tissue residue or similar contaminants. It is namely only in this way, that it would be possible to guarantee a sufficient introduction of current into the tissue to be treated. A falling temperature in the measured tissue area would, therefore, point to the conclusion that possibly the introduction of current is reduced despite an activated HF generator.

If an increase of the transfer resistance between the coagulation electrode and measured tissue area cannot be prevented with an increasing degree of coagulation (for example by the above-described measures, such as the adaptation of the electrode shape to the tissue), this must be taken into account appropriately in the determination of the final value for the target tissue introduction of energy. Preferably, the measuring device therefore comprises a device for measuring this transfer resistance so that a corresponding correction value can be included in the determination of the final value for the target tissue introduction of energy.

If only the detection of the voltage drop over the measured tissue area is to be used as the basis for further calculations, in practice, this method should be preferably used when the transfer resistance between the electrode and measured tissue is low or corresponding corrective measures can be taken. Only in this way can it be guaranteed that the voltage drop caused by the measured tissue area is determined correctly.

A preferred embodiment provides that the current-measuring device is designed in such a manner that the measured current can be transmitted to the control device so that this determines a phase relationship between the voltage and the current as a correction value. At higher frequencies, there is in particular an increase in the influence of capacitive reactances of the biological tissue, but capacitance and inductance of the leads are also noticeable at high frequencies. The influence of capacitance and inductance results in a phase displacement between the HF generator voltage and the HF current and hence also between the measured HF voltage and the HF current. Thus, a current measurement in addition to the voltage measurement enables the phase relationship between the voltage and the current to be determined and hence a more precise determination of the final value for the target tissue introduction of energy.

In addition, the phase displacement also changes when the resistance in the target tissue area changes due to the coagulation of the tissue. In this way, it is also possible to obtain data related to the coagulation of the tissue via a measurement of the phase displacement data.

The voltage-measuring device and the current-measuring device are provided in a preferred embodiment as modular building blocks in the HF surgical device. This means the measuring devices can be integrated permanently in the HF surgical device, or if required, removed.

A preferred embodiment provides that the control device is designed in such a manner that it transmits the shut-down signal to the HF generator so that this switches off and hence switches off the HF current. This provides a particularly simple and reliable embodiment for the deactivation of the HF surgical device.

In a preferred embodiment, at least one signal processing unit is provided to which the shut-down signal may be supplied. The signal processing unit is designed in such a manner that the shut-down signal may be used to control an optical and/or acoustic display in such a manner that the shut-down of the HF current due to the shut-down signal may be displayed for operator guidance. This display indicates the shut-down of the HF surgical device and hence the end of the coagulation process. A user can then terminate the coagulation process manually, for example. It is in principle possible for the display to be controlled directly by the control device.

The optical display can for example be designed as a screen so that this can indicate the shut-down of the HF current. The signal processing unit preferably also comprises a storage device which stores the shut-down signals, possibly together with various marginal conditions of earlier surgical interventions. These data can then be output on the screen. The empirical values shown make it possible to better evaluate previously found tissue structures with respect to an upcoming treatment. This will also simplify the selection of suitable electrosurgical instrument. The optical display can, for example, also be provides solely in the form of a lamp. The lamp lights up to indicate the end of the coagulation to the user and possibly also the shut-down of the HF current. A purely acoustic display indicates the end of the coagulation to the user without this having to be followed by an optical display. A combined optical and acoustic display is also possible.

Advantageously, the coagulation electrode is designed as a ball electrode. This is particularly suitable for interstitial coagulation, because the ball electrode initiates a substantially radially symmetrical current density distribution in the target tissue area, in particular with homogeneous tissue and when the distance from the coagulation electrode to the neutral electrode is large compared to the extension of the measured or target tissue area. Therefore, a one-dimensional measurement, e.g., of the voltage drop over the measured tissue area, allows conclusions to be drawn regarding the shape of the three-dimensional coagulation zone.

The coagulation electrode and the measuring electrode are arranged in such a manner in relation to each other that they measure the measured tissue area with respect to its extension at least in one dimension. This means that the distance between the coagulation electrode and the measuring electrode corresponds to the size of the measured tissue area in at least this one dimension. If a three-dimensional coordinate system were laid over the radially symmetrical extended measured tissue area, the zero point of this would correspond to a contact point of the coagulation electrode on the tissue to be treated. The coagulation electrode would therefore lie in the zero point of the coordinate system, while the measuring electrode would be arranged, for example on one of the axes of the coordinate system. This would mean the measured tissue area would be substantially measured in the one dimension, for example, with the detection of the voltage drop over the corresponding tissue area.

If the measured tissue area corresponds to the target tissue area (with a radially symmetrical extension), the desired coagulation zone would be measured in at least one direction. This is, for example, possible when the target tissue area is defined exactly, for example, by means of imaging techniques, before the actual operation.

In a preferred embodiment, the measuring device comprises two measuring electrodes arranged at a defined distance from the coagulation electrode, which may be brought into electrically conductive contact with the tissue to be treated. The measuring electrodes are hereby arranged along a line with the coagulation electrode on the electrosurgical instrument, wherein the coagulation electrode is arranged between the measuring electrodes. In the hypothetical three-dimensional coordinate system, the coagulation electrode is again arranged at its zero point, wherein the zero point corresponds to the contact point of the coagulation electrode on the measured tissue area. The first measuring electrode then lies, for example, on a positive axis and the second electrode on the corresponding negative axis. Therefore, the measured tissue area is measured one-dimensionally in two directions. The use of two measuring electrodes is in particular advisable with asymmetrical coagulation zones caused, for example, by non-spherical coagulation electrodes or by changes in tissue structure within the measured tissue area. The detection of a measured value in the measured tissue area, for example the detection of the voltage drop then takes place possibly via two voltage-measuring devices.

Preferably, the measuring electrode is arranged movably on the electrosurgical instrument. This will enable measured tissue areas or target tissue areas of different sizes to be measured with only one instrument. The measuring electrode is hereby designed displaceably and latchably or in other ways so that it may be placed at different places in the accommodation areas.

If the measuring electrode is fixed on the electrosurgical instrument, different electrosurgical instruments must be available for different sizes of measured tissue areas.

Thus, it is now possible to optimise the coagulation process in an extremely simple way and reduce the energy required for the devitalisation of the tissue.

The above description is primarily based on the detection of a voltage drop over the measured tissue area in order to draw conclusions regarding the required introduction of energy and hence the size of the coagulation zone. However, it is alternatively possible to determine the resistance or the change in resistance of the measured tissue area (possibly also of the target tissue area).

In the following description, the same reference numbers are used for the same parts and parts with the same function.

FIG. 1 shows an embodiment of the device according to the invention. FIG. 1 is a schematic diagram of the essential components of an HF surgical device 1 required for the explanation of the invention, namely an HF surgical device 10, a monopolar electrosurgical instrument 30 and a neutral electrode 33.

In the case of monopolar arrangements, as shown in FIG. 1, HF current supplied by a HF generator 11 to the electrosurgical instrument 30 is applied to tissue to be treated via a different electrode, here a monopolar coagulation electrode 31, wherein the current path leads through the body of a patient to the indifferent neutral electrode 33.

The HF surgical device 10 comprises an input port 12 for the connection of devices comprising finger and/or foot switches. These switching devices facilitate, for example, the activation and/or deactivation of the HF current. The switching devices are hereby preferably provided by means of a computer arrangement 50. Provided on the output side on the HF surgical device 10 are a first output port 13 and a second output port 14, by means of which the monopolar electrosurgical instrument 30 can be connected to the associated neutral electrode 33.

According to FIG. 1, the electrosurgical instrument 30 is embodied with a spherical coagulation electrode 31, wherein a measuring electrode 32 which may be brought into electrically conductive contact with the tissue to be treated is arranged on the electrosurgical instrument 30 at a defined distance r to the coagulation electrode 31 to measure the measured tissue area. The ball electrode 31 is connected to the HF generator 11 via the first output port 13. The measuring electrode 32 is also connected to the first output port 13, wherein a voltage-measuring device 20 is switched parallel between the coagulation electrode 31 and the measuring electrode 32. The neutral electrode 33 is connected to the second output port 14, wherein a current-measuring device 21 is connected in series between the neutral electrode 33 and the HF generator 11. Here, both the voltage-measuring device 20 and the current-measuring device 21 are integrated in the HF surgical device 10. As modular building blocks, the measuring devices may be permanently integrated in the HF surgical device 10 or if required can be also be occasionally removed.

The core of the HF surgical device 10 is the controllable HF generator 11 for generating an HF voltage and for supplying the HF current to the coagulation electrode 31 of the electrosurgical instrument 30. In this embodiment, the measuring electrode 32, the voltage-measuring device 20, the current-measuring device 21, a time-measuring device 22 and a temperature-measuring device 23, together with an arithmetic device 16 form a measuring device, wherein the voltage-measuring device 20 and the current-measuring device 21 are assigned to the arithmetic device 16 via control leads U and I and the temperature-measuring device 23 via a control lead θ. In this embodiment, the time-measuring device 22 is connected to the HF generator 11 and is also assigned to the arithmetic device 16 via a control lead T. The arithmetic device 16 is connected to a control device 15 via a control lead W. The HF generator 11 is also connected to the control device 15 via a control lead C. In addition, a signal processing unit 18 is connected to the control device 15 via a control lead C', wherein a display 19 is assigned to the signal processing unit 18.

FIG. 2 shows a section from the functional block diagram according to FIG. 1 in a simplified representation, wherein the tissue to be treated is also depicted. The electrosurgical instrument 30 and the tissue to be treated are substantially shown in section. The coagulation electrode 31 is introduced with the measuring electrode 32 into the tissue to be treated, wherein, at least in one direction, the two electrodes 31 and 32 define a measured tissue area 40, which is depicted as a subarea of a target tissue area 41. The target tissue area 41 and hence also the measured tissue area 40 lie as the tissue to be treated in surrounding tissue 42, which in turn should be exposed to the lowest possible current influence, but serves as a current path to the neutral electrode 33. Since the coagulation electrode 31 has a spherical design in this embodiment, the substantially radially symmetrical current density distribution results in a substantially radially symmetrical coagulation zone 41, in particular with homogeneous tissue and when the distance from the coagulation electrode 31 to the neutral electrode 33 is large compared to the extension of the measured or target tissue area. The monopolar electrosurgical instrument 30 with the ball electrode 31 according to FIG. 1 is provided, for example, for the interstitial devitalisation of tumour or metastatic tissue. For example, when treating a liver tumour, the electrode is inserted in the turnout in order to coagulate the surrounding tissue.

The following describes the mode of operation of the HF surgical device 1 according to the invention.

The coagulation electrode 31 is introduced together with the measuring electrode 32 into the tissue to be treated. The high-frequency current is supplied to the tissue to be treated via the coagulation electrode 31. In this case, the current density is divided substantially radially symmetrically in the tissue, since here a ball electrode is used. The measuring device is designed so that it detects at least one measured value u, i, t, θ describing an introduction of energy into the measured tissue area 40 effected via the coagulation electrode 31 in order to draw conclusions regarding possible energy losses which could reduce the total introduction of energy into the tissue to be treated. The measured value to be detected can, for example, be detected as a voltage drop u which can be measured via the measured tissue area 40, wherein the voltage drop in the tissue lying between the coagulation electrode 31 and the measuring electrode 32 can be detected with the aid of the measuring electrode 32 and the voltage-measuring device 20 switched in parallel between the electrodes 31 and 32 by means of a measuring lead. The measuring electrode 32 serves therefore as a contact surface for the tissue to be treated and so delimits the measured tissue area 40 and lies in the current path to the neutral electrode 33. If the current i through the measured tissue area 40 can, as described above, be detected with conventional technology in the surgical device, the voltage drop u may be used, for example, to determine the power input into the measured tissue area 40. This means that the voltage drop u in the measured tissue area 40 is measured by means of the measuring electrode 32 (and displayed via the voltage-measuring device 20), wherein the arithmetic device 16 determines from this (using the corresponding power value) the corresponding power input, for example. The detection of the voltage drop u via only one selected area of the measured tissue area is possible due to the radially symmetrical extension of the target tissue area 41. The power input can in turn then be used to draw conclusions regarding the introduction of energy required for the target tissue area, for example.

Therefore, a measured value characteristic for the measured tissue introduction of energy—the voltage drop u—used to determine an introduction of energy in order to control or regulate the HF generator in such a manner that the introduction of energy required for the optimum coagulation result into the target tissue area is achieved by matching the introduced energy to the preset, possibly determined final value for the target tissue introduction of energy into the target tissue area.

The determination of the introduction of energy into the measured tissue area is also necessary because unavoidable energy losses, for example thermal losses, through the tissue areas surrounding the measured tissue area or the target tissue area (ultimately to a neutral electrode) or even an electrical power loss, caused, for example, by stray currents, cannot readily be detected. Namely, due to these losses, the total introduction of energy introduced by the coagulation electrode is not fully available for the target tissue area. The measuring device shown here is designed to at least 'measure' the measured tissue so that it is possible in the end to evaluate how much introduction of energy is retained for the target tissue area and is still required for an optimal coagulation result, for example.

FIG. 3 shows an equivalent circuit diagram, which illustrates the current path during the treatment of a patient by means of coagulation and the resistances lying in the current path which, in addition to the target tissue area 41, cause the above-described losses. A resistance $R_Z$ of the target tissue area 41 is made up of a resistance $R_M$ of the measured tissue area and a saturation resistance $R_R$ of the remaining target tissue area. The resistances $R_M$ and $R_Z$ should be understood as being in series with a patient resistance $R_P$. Here, the term 'patient resistance' means the tissue which is not to be treated but available as a current path between the target tissue area and the neutral electrode and possibly a further transfer resistance between this tissue and neutral electrode attached to the patient. Under unfavourable coagulation conditions, when determining the final value w for the target tissue introduction of energy, consideration should also be paid to a transfer resistance $R_0$ between the coagulation electrode 31 and the tissue to be treated, which is responsible for further losses from the total introduction of energy. For this, the HF surgical device 10 preferably comprises a device (not shown here) for the detection of the transfer resistance $R_0$.

The detection of the measured value in the explicit measured tissue area 40 (instead of directly in the target tissue area 41) is used to simplify the measurement. In this way, the electrodes 31, 32 can be introduced independently of the dimensions of the target tissue area 41 into the tissue to be treated, i.e., coagulation electrode 31 and measuring electrode 32 do not have to be arranged at a distance in such a manner that they detect the defined target tissue area 41 exactly. In a special case, however, the measured tissue area 40 'to be measured' corresponds to the target tissue area 41 so that the introduction of energy also corresponds to the target tissue introduction of energy.

On the basis of the at least one measured value u (and losses detected therewith) and on the basis of available empirical values, a set value or final value w for the target tissue introduction of energy into the target tissue area 41 required for an optimal coagulation result is determined. The arithmetic device 16 is, for example, designed to determine this final value w. This means that the measuring device is always designed in such a manner, that it provides the arithmetic device with the required measured values to calculate or determine the performed and required introduction of energy, possibly based on empirical values. The final value w for the target tissue introduction of energy is in principle pre-specified, since it is based, for example, on empirical values or determined from current tissue parameters. In principle, the final value for the target tissue introduction of energy may be determined from the value measured in the measured tissue area, here the voltage u, and the known current i, e.g., by extrapolation. This is particularly possible if the measured tissue area corresponds to the target tissue area. To make a current regulation more precise, however, it is advisable, in practice, to perform the determination of the final value w at least additionally with reference to empirical values. The empirical values are available, for example, from earlier interventions and allow for known tissue parameters. Hence, final values w may be pre-specified as set values to which the introduction of energy into the measured tissue area 40 as an instantaneous actual value is to be matched by the current regulation (control) wherein the measured tissue introduction of energy is in a functional relationship with an actual value for the measured size (from which the actual value of the measured tissue introduction of energy is obtained). The latter is in particular recommended if the measured tissue area 40 differs from the target tissue area 41.

On the basis of the determined and/or preset final value w, the required HF current is supplied to the tissue to be treated via the coagulation electrode 31 until the optimum introduction of energy in the tissue to be treated, i.e., the final value w, is achieved. The control device 15 then generates a shut-down signal c when the final value w is reached to indicate that the coagulation process has ended at an optimum time. In the simplest case, the shut-down signal is generated when the measured value, that is, the voltage drop for example, has reached a specific value—based on empirical values. In this simplest case, the HF generator 11 is controlled in such a manner by the control device 15 that it shuts down in response to the shut-down signal c. The detection or determination of the final value w for the introduction of energy into the target tissue area 41 required for optimum coagulation, here via the measured tissue area 40, facilitates the precise treatment of the defined tissue, wherein the surrounding tissue 42 is protected to the maximum degree.

The arithmetic device 16 is preferably designed in such a manner that the required final value w is repeatedly redetermined in defined time intervals. In this way, the final value w is pre-specified in accordance with a fixed time sequence of a time-program control. The time-program control is required, for example, if the tissue area to be treated is to be observed during the coagulation process and its tissue changes taken into account or when it is already known from experience that the set value requires constant adjustment during coagulation. The changing tissue parameters during coagulation form the basis for the further course of the coagulation. This means that the optimum final value w for the target tissue introduction of energy can change during the course of the coagulation in such a manner that the repeated redetermination of the final value, which the actual value should follow, is required.

The time-program control can alternatively be provided in such a manner that a fixed time-program control is specified in advance, for example on the basis of empirical values, wherein the course of the coagulation in the tissue to be treated, for example, is not taken into consideration. A combination of current tissue parameters with preset empirical values is also advisable to achieve an optimal introduction of energy into the tissue to be treated, that is, into the target tissue area.

A time-program control is a simple way of facilitating the regulation of the power input and hence of the introduction of energy, taking into account the tissue changes or expected tissue changes.

If it is necessary to determine not only the power introduced into the tissue but also a duration t over which the power input take place, the duration t can be detected with the aid of the time-measuring device 22. In the simplest case, the time-measuring device 22 detects the relevant activation phases of the HF generator 11, that is, for example, the duration of the power supply into the tissue to be treated. In this way, the duration that the HF current was supplied to the tissue to be treated is determined so that the measured tissue introduction of energy into the measured tissue area 40 can be determined indirectly from the measured values (current, voltage and time) as the power and/or work introduced over time (in the case of thermal devitalisation by the HF current, the amount of energy corresponds to the converted electrical power integrated in the measured or target tissue area over time). To do this, the time-measuring device 22 supplies the corresponding duration t to the arithmetic device 16 via the control lead T. The detection of the temporal course of the introduction of energy is also advantageous in that this takes into account different power inputs with different time characteristics. Therefore, the level of the power in dependence on the duration of the introduction is used as a basis so that the course of the coagulation can be calculated more accurately.

For tracking the amount of heat introduced into the measured tissue area 40, it may be useful to observe any temperature change in the measured tissue area 40. For this, the measuring device comprises the temperature-measuring device 23 for measuring a tissue temperature $\theta$ in the measured tissue area, which is transmitted to the arithmetic device 16 via the control lead $\theta$. The measuring device is designed in such a manner that the measured tissue introduction of energy can be determined and/or corrected in dependence on the measured temperature $\theta$. In particular, the observation of the temperature may be used, for example, to draw conclusions regarding a suitable or unsuitable power input or introduction of energy and also regarding the degree to which the tissue has reached a temperature suitable for devitalisation. These data simplify and make more precise the determination of the final value for the target tissue introduction of energy. It is advantageous to use at least two temperature-measuring devices in order to understand a temperature gradient in the tissue to be treated.

As already mentioned, the final value w for the target tissue introduction of energy into the target tissue area may be determined, for example, by extrapolation or by extrapolation supported by empirical values. Empirical values are also required in order to draw conclusions from the measured tissue area regarding possible energy losses. The measuring device is therefore assigned to the storage device 17 for the storage of experimentally determined series of measurements describing comparative sample tissue. Then, in addition to a general extrapolation, the determination of the final value w is based on the stored series of measurements. For example, thermal capacities or thermal conductivities enable conclusions to be drawn regarding the coagulation behaviour of the tissue to be treated.

A further (not shown) measuring device, which is also assigned to the control device 15, alternatively facilitates the measurement of the tissue to be treated. This enables the characteristic measured values for the tissue to be treated to be entered directly into the storage device 17. In addition, the tissue to be treated can be used directly for the above-described time-program control so that new final values w for the target tissue introduction of energy (set values) are obtained from changing tissue parameters during the coagulation. To facilitate the input of the tissue parameters, the storage device 17 is also assigned the input unit 50, which is designed in such a manner that a user can enter the measured values describing a comparative sample tissue and/or known tissue parameters for storage in the storage device 17. Preferably, the above-described further measuring device is designed in such a manner that the measured values detected on the tissue to be treated are automatically entered into the storage device 17.

In the case of a spherical electrode and hence a radially symmetrical coagulation zone 41, a one-dimensional measurement (in the direction of the coagulation electrode 31 with a measuring electrode 32) of the voltage drop over the measured tissue area 40 allows conclusions to be drawn regarding the shape of the three-dimensional coagulation zone 41. In the case of asymmetrical coagulation zones, such as could result, for example, from non-spherical coagulation electrodes, for the reliable detection or determination of at least one dimension of coagulation zone 41, at least two measuring electrodes 32, 32' should be arranged on the electrosurgical instrument 30 in two opposing directions, based on the coagulation electrode 31. For this, as shown in FIG. 2, the measuring electrodes 32, 32' and the coagulation electrode 31 are arranged along a line wherein the coagulation electrode 31 is arranged between the measuring electrodes 32, 32'. The detection of the measured value of the voltage drop u over the measured tissue area 40 is then performed via two voltage-measuring devices.

Preferably, the measuring electrode 32, 32' is arranged movably on the electrosurgical instrument 30. This enables measured tissue areas 40 or target tissue areas 41 of different sizes to be measured with only one instrument. The measuring electrode 32, 32' can have a movable and latchable design or it may be accommodated in different locations in the reception areas.

If the measuring electrode 32, 32' is fixed on the electrosurgical instrument 30, different electrosurgical instruments are provided for measured tissue areas of different sizes.

As shown in FIGS. 1 to 3, the HF surgical device 1 comprises the above-described current-measuring device 21. The measurement of the HF current facilitates the determination of a phase relationship between the current and voltage, for example, with the aid of the control device 15. At higher frequencies, there is, in particular, an increase in the influence of capacitive reactances of the biological tissue, though the capacitance and inductance of the supply leads are evident at high frequencies. The determination of the phase relationship between the voltage and current permit a more precise determination of the final value w for the target tissue introduction of energy.

According to FIG. 1, the HF surgical device 10 comprises the aforementioned signal processing unit 18 to which the shut-down signal c may be supplied via the control lead C'. The signal processing unit 18 is designed in such a manner that it transmits the shut-down signal c to the optical and/or acoustic display 19 so that the shut-down of the HF current due to the shut-down signal c may be displayed for operator guidance. A purely acoustic display indicates the end of the coagulation to the user without this having to be followed by an optical display. A combination of optical and acoustic displays is also possible.

The optical display can be embodied as a display and/or, for example, as a lamp. The signal processing unit 18 preferably comprises a storage device (not shown), which stores the shut-down signals (including various boundary conditions) of earlier surgical interventions. The data may be displayed on the screen 19 so that the operator can use empirical values from earlier interventions for an upcoming intervention.

As already described, the measured value to be detected can be the voltage dropping through the measured tissue area 40. It is, however, also possible, to detect the resistance or the change in resistance of the measured tissue area 40 (possibly of the target tissue area 41) during its coagulation, in order to determine therefrom a relationship with the expected size of the coagulation zone.

The invention may be used for both coagulation processes and cutting processes. It may, in particular, be of advantage to detect the coagulation effect occurring with the cutting processes according to the invention. The subject matter according to the invention can also provide reliable detection and monitoring of electrosurgical treatments with bipolar arrangements.

Reference is made at this point to the fact that all the above-described parts that are claimed as essential for the invention individually and in any combination are shown in the drawings. A person skilled in the art will be familiar with modifications thereof.

The invention claimed is:

1. A high-frequency surgical device for the monopolar coagulation of biological tissue using a high-frequency current, comprising:
    an electrosurgical instrument with a coagulation electrode;
    a neutral electrode; and
    a high-frequency surgical apparatus comprising:
        a high-frequency generator for generating a high-frequency voltage and for supplying the high-frequency current to the coagulation electrode of the electrosurgical instrument;
        a measuring device to detect at least one measured value describing a measured tissue introduction of energy into a defined measured tissue area effected via the coagulation electrode; and
        an arithmetic device to determine the measured tissue introduction of energy into the defined measured tissue area and to determine a final value to be used as a preset for the coagulation process for a target tissue introduction of energy into a target tissue area,
        wherein at least one control device is provided for stopping the coagulation process as soon as the target tissue introduction of energy reaches the final value, so that said high-frequency current is supplied to the tissue to be treated until the final value is reached and is configured to control or regulate the high-frequency generator based on the final value so that the required high-frequency current is supplied to the target tissue area, and to generate a shut-down signal for stopping the coagulation process as soon as the target tissue introduction of energy reaches the final value, so that said high-frequency current is supplied to the tissue to be treated until the final value is reached
    wherein the measuring device comprises:
        at least one measuring electrode arranged at a defined distance from the coagulation electrode, the at least one measuring electrode configured to be in electrically conductive contact with tissue in the measured tissue area; and
        at least one voltage-measuring device for measuring a voltage drop over the measured tissue area independent of any line losses, wherein the voltage drop is the difference between the electric potential of the measuring electrode and the electric potential of the coagulation electrode created by the applied voltage between the coagulation electrode and the neutral electrode, and
        wherein a power introduced into the measured tissue area is determined from the measured values to determine the final value for the target tissue introduction of energy.

2. The high-frequency surgical device according to claim 1, wherein the arithmetic device redetermines the final value for the target tissue introduction of energy at defined time intervals in accordance with a fixed time sequence in a time-program control.

3. The high-frequency surgical device according to claim 1, wherein the arithmetic device reads the final value for the target tissue introduction of energy from a preset set value progression according to a fixed time sequence in a time-program control.

4. The high-frequency surgical device according to claim 1, wherein the measured tissue area is smaller than the target tissue area.

5. The high-frequency surgical device according to claim 1, wherein the measuring device further comprises:
    at least one current-measuring device for measuring the high-frequency current in the measured tissue area to determine the final value for the target tissue introduction of energy.

6. The high-frequency surgical device according to claim 5, wherein the measuring device further comprises:
    at least one first time-measuring device for measuring a duration of the current flow into the measured tissue area to determine the final value for the target tissue introduction of energy.

7. The high-frequency surgical device according to claim 6, wherein the measuring device further comprises
    at least one second time-measuring device for measuring a duration of the measured tissue introduction of energy into the measured tissue area, the final value for the target tissue introduction of energy being determined from the duration of the measured tissue introduction of energy.

8. The high-frequency surgical device according to claim 5, wherein the current-measuring device transmits the detected current to the control device for determination of a phase relation between the voltage and the current, the phase relation used as a correction value.

9. The high-frequency surgical device according to claim 5, wherein
the current-measuring device is a modular building block of the high-frequency surgical device.

10. The high-frequency surgical device according to claim 1, further comprising
a storage device assigned to the measuring device for the storage of experimentally determined measured values describing comparative sample tissue, the experimentally determined measured values being used to determine the final value for the target tissue introduction of energy.

11. The high-frequency surgical device according to claim 10, wherein
the measuring device makes measurements of thermal capacities and/or thermal conductivities to be used in the determination of the final value for the target tissue introduction of energy.

12. The high-frequency surgical device according to claim 11, further comprising
an additional measuring device, controlled by the control device, for storing as comparative values in the storage device measured values describing the tissue to be treated.

13. The high-frequency surgical device according to claim 12, further comprising
an input unit assigned to the control device, for allowing a user to enter the measured values describing the comparative sample tissue and/or known tissue parameters for storage in the storage device.

14. The high-frequency surgical device according to claim 11, further comprising an input unit assigned to the control device, for allowing a user to enter the measured values describing the comparative sample tissue and/or known tissue parameters for storage in the storage device.

15. The high-frequency surgical device according to claim 10, wherein
the measuring device further comprises at least one temperature-measuring device for measuring a tissue temperature in the measured tissue area, the final value for the target tissue introduction of energy being determined and/or corrected based on the measured temperature and the stored measured values.

16. The high-frequency surgical device according to claim 10, further comprising an additional measuring device, controlled by the control device, for storing as comparative values in the storage device measured values describing the tissue to be treated.

17. The high-frequency surgical device according to claim 10, further comprising an input unit assigned to the control device, for allowing a user to enter the measured values describing the comparative sample tissue and/or known tissue parameters for storage in the storage device.

18. The high-frequency surgical device according to claim 1,
wherein the measuring device comprises a device for measuring a transfer resistance between the coagulation electrode and the measured tissue area, the transfer resistance being a correction value for the determination of the final value for the target tissue introduction of energy.

19. The high-frequency surgical device according to claim 1, wherein
the voltage-measuring device is a modular building block of the high-frequency surgical device.

20. The high-frequency surgical device according to claim 1, wherein
the control device transmits the shut-down signal to the high-frequency generator so that the high-frequency generator switches off and hence switches off the high-frequency current.

21. The high-frequency surgical device according to claim 20, further comprising
at least one signal processing unit to which the shut-down signal is supplied, the signal processing unit using the shut-down signal to control an optical and/or acoustic display so that the switching off of the high-frequency current due to the shut-down signal is displayed for operator guidance.

22. The high-frequency surgical device according to claim 1, wherein
the coagulation electrode is a ball electrode.

23. The high-frequency surgical device according to claim 1,
the measuring device comprising two measuring electrodes arranged at a defined distance from the coagulation electrode, the two measuring electrodes configured to be in electrically conductive contact with the tissue to be treated, the measuring electrodes and the coagulation electrode being arranged in a line with the coagulation electrode being between the two measuring electrodes.

24. The high-frequency surgical device according to claim 1, wherein
the measuring electrode is arranged movably on the electrosurgical instrument.

25. A method of coagulating a target biological tissue, the method comprising:
applying a high-frequency current to a coagulation electrode;
using the coagulation electrode to apply energy to a measured tissue;
measuring at least one variable indicative of the applied energy effected by the coagulation electrode in the measured tissue using a measuring electrode, wherein the at least one variable comprises the voltage drop between the electric potential of the measuring electrode and the electric potential of the coagulation electrode created by the applied voltage between the coagulation electrode and a neutral electrode;
determining a final applied energy amount for coagulating the target tissue based on the measured at least one variable indicative of the applied energy effected by the coagulation electrode; and
automatically stopping the application of the high-frequency current as soon as the final applied energy amount is applied to the target tissue, so that said high-frequency current is supplied to the tissue to be treated until the final applied energy amount is reached.

* * * * *